US012654362B2

(12) United States Patent
Bellio et al.

(10) Patent No.: US 12,654,362 B2
(45) Date of Patent: Jun. 16, 2026

(54) DEODORIZATION APPARATUS AND METHOD

(71) Applicant: PIOVAN S.P.A., Santa Maria di Sala (IT)

(72) Inventors: Enrico Bellio, Ponzano Veneto (IT); Davide Cappellini, Soncino (IT)

(73) Assignee: PIOVAN S.P.A., Santa Maria di Sala (IT)

( * ) Notice: Subject to any disclaimer, the term of this patent is extended or adjusted under 35 U.S.C. 154(b) by 726 days.

(21) Appl. No.: 18/012,523

(22) PCT Filed: Jul. 23, 2021

(86) PCT No.: PCT/IB2021/056666
§ 371 (c)(1),
(2) Date: Dec. 22, 2022

(87) PCT Pub. No.: WO2022/023905
PCT Pub. Date: Feb. 3, 2022

(65) Prior Publication Data
US 2023/0264390 A1 Aug. 24, 2023

(30) Foreign Application Priority Data

Jul. 28, 2020 (IT) ........................ 102020000018208
Jul. 28, 2020 (IT) ........................ 102020000018220
(Continued)

(51) Int. Cl.
*B29B 13/02* (2006.01)
*A61L 9/16* (2006.01)
(Continued)

(52) U.S. Cl.
CPC .............. *B29B 13/021* (2013.01); *A61L 9/16* (2013.01); *B29B 9/16* (2013.01); *B29B 13/065* (2013.01);
(Continued)

(58) Field of Classification Search
CPC ....... B29B 13/021; B29B 9/16; B29B 13/065; B29B 2009/161; B29B 2009/168;
(Continued)

(56) References Cited

U.S. PATENT DOCUMENTS 4,543,367 A 9/1985 Rutherford et al.
2002/0004995 A1 1/2002 France et al.
(Continued)

FOREIGN PATENT DOCUMENTS

CA 2548699 A1 * 8/2007 .............. F24F 11/77
CN 206870187 U 1/2018
(Continued)

OTHER PUBLICATIONS

"NAUMAN", Ind. Eng. Chem. Res, "Residence Time Theory" (Year: 2008).*
(Continued)

*Primary Examiner* — Brendan A Hensel
(74) *Attorney, Agent, or Firm* — Oliff PLC

(57) ABSTRACT

A deodorization method and apparatus are disclosed to eliminate, reduce or correct the odour of incoherent plastics, i.e. in the form of granules and/or microgranules and/or powder and/or flakes or the like, with a container of the incoherent plastics, an actuator for generating a process gas flow from a gas inlet to a gas outlet of said container, an olfactory sensor arranged to detect odorous emissions in the process gas exiting from said container, a controller configured to control at least one parameter of the process gas on the basis of an odour intensity measured by said olfactory
(Continued)

| COMPOUND | $P_{sat}$ (KPa, 25°C) | $OT_{air}$ (ppm) | O.I. (25°C) |
|---|---|---|---|
| 2-octanone | 0.10 | 250 | 4 |
| Ethanol | 7.87 | 6000 | 13 |
| Toluene | 3.79 | 40 | 947 |
| Acetone | 30.8 | 300 | 1030 |
| 1-pentanol | 0.26 | 1 | 2590 |
| Hexane | 20.2 | 64 | 3160 |
| 2-butanone | 12.6 | 30 | 4200 |
| Propene | 1190 | 80 | 149000 |
| Hexanal | 1.48 | 0.0094 | 1574500 |
| Pentanal | 4.58 | 0.02 | 2290000 |
| Carbon disulfide | 48.2 | 0.21 | 2295000 |
| 1-hexene | 24.8 | 0.02 | 12400000 |
| Dimethyl disulfide | 3.82 | 0.0014 | 27280000 |
| Dimethyl sulfide | 64.4 | 0.0014 | 460000000 |
| Methanethiol | 203 | 0.0021 | 961900000 |
| Hydrogen sulfide | 2020 | 0.0047 | 4297870000 | sensor, with the aim of eliminating the substances that cause undesired odours from the incoherent plastics that is usable in a transformation process to make an end product.

16 Claims, 5 Drawing Sheets

(30)          Foreign Application Priority Data

| Jul. 28, 2020 | (IT) | ........................ | 102020000018226 |
| Jul. 28, 2020 | (IT) | ........................ | 102020000018232 |

(51) Int. Cl.

| *B29B 9/16* | (2006.01) |
| *B29B 13/06* | (2006.01) |
| *B29C 71/02* | (2006.01) |
| *F26B 1/00* | (2006.01) |

(52) U.S. Cl.
CPC ............ *C08J 7/08* (2013.01); *A61L 2209/111* (2013.01); *B29B 2009/161* (2013.01); *B29B 2009/168* (2013.01); *F26B 1/00* (2013.01)

(58) Field of Classification Search
CPC .... B29B 7/66; B29B 7/72; B29B 7/78; B29B 7/82; A61L 9/16; A61L 2209/111; C08J 7/08; F26B 1/00; C08F 6/005; C08F 6/28
See application file for complete search history.

(56)               References Cited

U.S. PATENT DOCUMENTS

| 2004/0132964 A1 | 7/2004 | Mulgrew et al. |
| 2008/0185758 A1 | 8/2008 | Damme |
| 2010/0180667 A1 | 7/2010 | Bender et al. |
| 2020/0298449 A1* | 9/2020 | Thepsimuang ......... B01F 29/40 |

FOREIGN PATENT DOCUMENTS

| CN | 108771767 A | * | 11/2018 | ............... A61L 9/22 |
| CN | 209534221 U | | 10/2019 | |
| CN | 111349336 A | * | 6/2020 | ............... B29B 7/66 |
| EP | 2 635 609 B1 | | 9/2019 | |
| GB | 1201354 A | | 8/1970 | |
| JP | 2004082925 A | * | 3/2004 | ........... B60H 3/0035 |

OTHER PUBLICATIONS

Oct. 20, 2021 International Search Report issued in International Patent Application No. PCT/IB2021/056666.
Oct. 20, 2021 Written Opinion of the International Searching Authority issued in International Patent Application No. PCT/IB2021/056666.
Barkó, György et al. "Application of an artificial neural network (ANN) and piezoelectric chemical sensor array for identification of volatile organic compounds". Talanta, 44, 1997, pp. 2237-2245.

* cited by examiner

| COMPOUND | $P_{vap}$ (KPa, 25°C) | $OT_{low}$ (ppm) | O.I. (25°C) |
|---|---|---|---|
| 2-octanone | 0.10 | 250 | 4 |
| Ethanol | 7.87 | 6000 | 13 |
| Toluene | 3.79 | 40 | 947 |
| Acetone | 30.8 | 300 | 1030 |
| 1-pentanol | 0.26 | 1 | 2590 |
| Hexane | 20.2 | 64 | 3160 |
| 2-butanone | 12.6 | 30 | 4200 |
| Propene | 1190 | 80 | 1490000 |
| Hexanal | 1.48 | 0.0094 | 1574500 |
| Pentanal | 4.58 | 0.02 | 2290000 |
| Carbon disulfide | 48.2 | 0.21 | 2295000 |
| 1-hexene | 24.8 | 0.02 | 12400000 |
| Dimethyl disulfide | 3.82 | 0.0014 | 27280000 |
| Dimethyl sulfide | 64.4 | 0.0014 | 460000000 |
| Methanethiol | 202 | 0.0021 | 961900000 |
| Hydrogen sulfide | 2020 | 0.0047 | 4297870000 |

Fig. 1

DEODORIZATION APPARATUS AND METHOD

BACKGROUND OF THE INVENTION

The invention relates to a deodorization method and/or a deodorization apparatus, in particular for deodorizing incoherent plastic material, i.e. plastics in the form of granules and/or microgranules and/or powder and/or flakes or the like.

In this description, for deodorization or deodoration, means a suitable process for eliminating, reducing or correcting an odour of a substance.

The invention can be applied in the sector of a plant for treating incoherent plastics, such as for example a plant for dehumidification and/or drying and/or crystallization and/or vacuum conveying and/or pressure conveying of incoherent plastics. This treatment plant can be intended, in particular, to supply a user machine, such as for example a machine for processing and transforming plastics, in particular an extruder that supplies extruded plastics to an injection and/or blow and/or compression moulding apparatus.

In the sector of the transformation of the plastics into an end product, in certain cases limiting, annulling or correcting the odour of the end product is required. Think, for example, of the specific case of the production of parts for the interiors of motor cars. In fact, not all purchasers appreciate the characteristic odour of a new automobile, which is normally emitted by the resin with which the interior parts are made, and which is not easily eliminable.

Further, in the sector of treating plastics, it is known to make end products with polymer granules obtained from recycling, to be mixed in a variable percentage with virgin resin. The recycling granules, even if they are selected and treated beforehand, generally emit an acrid and unpleasant odour in the subsequent transformation processes, in particular when the granules are melted. This odour is usually not detectable at environmental temperature or in given environmental conditions, because the odorous emissions are not always released.

It is also known that some products made of plastics release into the air over time odorous emissions, which in certain cases can also contain oily particles that are dispersed into the environment or adhere to adjacent surfaces, thus transmitting the odour.

An odour can in fact be detected when a gaseous molecule dissolves in the olfactory mucous and succeeds in binding with a receptor. The substances that are able to product an odorous sensation must accordingly be able to emit vapours. For this reason, the volatility of compounds, which are quantifiable in terms of vapour pressure, is a parameter in estimating the ability of a substance to cause an odour. One parameter indicating the ability of a single substance to spread odour is the so-called Odour Index (OR.I.), which is defined as the (adimensional) ratio between the vapour pressure of the odorous substance (expressed in ppm, assuming that 1 atmosphere corresponds to $10^6$ ppm), and the minimum concentration (expressed in ppm) perceptible by 100% of the panels selected for the analysis: OR.I.=pap OT100.

The OR.I. parameter enables indications to be provided on one hand of very odorous substances but with low vapour pressure, and on the other hand of substances with high vapour pressure and weak odorous sensations. In general, it is possible to consider as potentially hardly odorous a compound with an OR.I. below $10^5$, like for example alkanes and some ketones, whereas sulphur compounds, such as mercaptans (e.g. isopropylmercaptan), can reach OR.I. values of $10^9$. In the table of FIG. 1 the OR.I. values are shown for certain odorous substances.

The prior art includes various odour monitoring devices, for example, olfactory sensors, also called electronic noses or IOMS (Instrumental Odour Monitoring Systems), for measuring odorous emissions. According to the sensorial technique of dynamic olfactometry, the odour concentration is generally expressed in odour units per cubic metre (OU/$m^3$). The analysis of samples of substance by dynamic olfactometry is regulated by UNI EN 13725:2004 on the concentration of odours. Specifically, technical standard UNI EN 13725, defines as a European odour unit (ouE) the quantity of odour/s that, when evaporated in 1 $m^3$ of neutral gas in normal conditions (standard ambient temperature and pressure or SATP conditions, in general temperature=298.15 K=25° C. and pressure 100 kPa=1 bar), causes a given physiological response (detection threshold) from a test unit, i.e. an equivalent physiological response to the response caused by a European Reference Odour Mass (or EROM) evaporated into 1 $m^3$ of neutral gas in normal conditions. The 1 EROM value is the mass of substance that has evaporated into 1 $m^3$ of neutral gas in normal conditions and which causes a physiological response D50 (detection threshold), evaluated by a test group of odour experts in conformity to this standard. In this situation, by definition, a concentration of 1 ouE/$m^3$ is obtained. For the reference odour n-butanol (No CAS 71-36-3), 1 EROM corresponds to a 123 µg mass that, evaporated into 1 $m^3$ of neutral gas, in normal conditions, produces a concentration of 0.040 µmol/mol (fraction by volume of 40 parts per billion). A relation was defined for the ouE for the reference odour and the ouE for each mixture of odours, with reference to the physiological response D50 (detection threshold al 50%): 1 EROM≡123 µg for the n-butanol=1 ouE (European Odour Unit) for the mixture of odours. This relation enables the odour concentrations of each odour substance to be expressed in terms of "mass equivalents of the n-butanol". The odour concentration can be evaluated in relation to a concentration of 1 ouE/$m^3$. In practice, the odour concentration, expressed in ouE/$m^3$, can be substantially used as a mass concentration (kg/$m^3$) (UNI EN 13725, 2003).

In general, prior art olfactory sensors do not identify the single chemical components of a gas but recognize an odour by comparing the odour with a preset set of odours, for example to distinguish an expired foodstuff from a well conserved foodstuff, and measures the intensity of the recognized odour. An olfactory sensor, or electronic nose, is distinguished from other measuring instruments through its ability to recognize and identify an odour emission of a gas mixture without performing a detailed analysis of the chemical composition of the mixture.

It is further known that there are some significant similarities in the chemical structure of the molecules responsible for the same categories of odour. For example, compounds with a fish odour in general contain a nitrogen atom linked to another three atoms (like dimethylamine CH3-NH-CH3 and ethylamine H2N-CH2CH3). It is also known that very small differences in the structure of a molecule can lead to significant differences in odour. In this regard, about 250 pairs of enantiomers with significantly different odours have been identified, although they are almost identical structurally. It is further known that a large variety of different molecular structures are reducible to a single odour, for example the odour of musk. It is in particular possible to describe an odorous substance through five parameters:

perceived olfactory threshold and concentration, intensity, diffusibility or volatility, quality, hedonic tone.

The prior art includes olfactory sensors including metal oxide semiconductors known as MOS. An olfactory sensor of known type may include for example, a set of sensors selected to detect the presence of predefined molecules, for example volatile organic compounds (VOC), hydrocarbons, alcohols, etc. It is known that the variation of conductivity of an oxide in the presence of volatile organic compounds (VOC), with respect to the conductivity in a reference condition, is due to an irreversible reaction between the odour and the types of oxygen adsorbed on the surface of the semiconductor. This reaction consumes oxygen and frees the electronics that were linked to the oxygen ions, lowering the resistance of the sensor. The resistance increases if the sensor is exposed to an oxidizing gas, like nitrogen dioxide, as the gas is adsorbed in the form of negative ions on the surface of the semiconductor.

Patent publications CN 206870187 U and CN 209534221 U disclose two known embodiments of deodorizing apparatuses. Patent publication CN 111349336 A discloses a deodorization apparatus according to the preamble of claim 1.

Various aspects of the prior art are improvable. Firstly, it is desirable to make end products made of plastics that do not release undesired odorous emissions. Secondly, it is desirable to prevent the molecules associated with any desired odour remaining trapped in the structure of the product in the processes of transforming polymeric resins to make an end product.

SUMMARY OF THE INVENTION

One object of the invention is to remedy one or more of the aforesaid limits and drawbacks of the prior art.

One object is to provide an alternative apparatus and/or method to the prior art for deodorizing plastics.

One object is to make a product made of plastics in which emanations of undesired odours are eliminated or significantly reduced.

One object is to deodorize a polymer resin in incoherent format, i.e. in granules and/or microgranules and/or powder and/or flakes or the like.

One advantage is to eliminate or reduce the substances that cause undesired odours from the incoherent plastic material (polymer granules) usable in the transformation processes that are suitable for making an end product.

One advantage is to permit a measurement of the quantity of residual odour and/or the quantity of odour extracted from a deodorized polymer resin.

One advantage is to control safely and reliably the deodorization process for deodorizing polymer granules, in particular virgin granule obtained from the raw material and/or granule obtained from the recycled material.

Such objects and advantages, and still others, are achieved by a method and/or an apparatus according to one or more of the following claims.

In one embodiment, a deodorization apparatus includes a container of incoherent plastics, an actuator for generating a process gas flow from an inlet to an outlet of said container, an olfactory sensor arranged to detect odorous emissions in the process gas exiting from said container, a controller configured to adjust at least one process parameter, in particular a parameter relating to the process gas, such as the flow of the process gas and/or the temperature of the process gas entering the container, on the basis of an odour intensity measured by said olfactory sensor.

In one embodiment, a deodorization apparatus includes a hopper for containing the plastics in granules to be treated, a fan to generate a flow of a process gas through the inside of the hopper, at least one temperature sensor for detecting a temperature of the process gas, at least one olfactory sensor to detect the odorous emissions of the process gas exiting from the hopper, at least one flowrate sensor (in mass and/or volume) of the process gas, at least one sensor for detecting the level of filling of the hopper, at least one device for detecting the deodorization process time, and a control unit configured to receive, process and store the signals of the sensors and to adjust at least one process parameter, in particular a parameter relating to the process gas, as a function of the signals supplied by the aforesaid olfactory sensor, so as to eliminate the odour of the plastics.

In one embodiment, a deodorization method includes the steps of generating a flow of a process gas that flows from an inlet to an outlet of a container that contains incoherent plastics and heating the process gas to a set temperature so that the flow of the heated process gas removes from the incoherent plastics the molecules that determine an undesired odour.

In one embodiment, a deodorization apparatus includes a container, a device for generating a process gas that flows through the inside of the container, an agitator arranged for stirring incoherent plastics contained in the container, and a controller configured to control the agitator on the basis of signals supplied by an olfactory sensor arranged to detect odorous emissions of the process gas.

In one embodiment, a deodorization method includes the steps of introducing incoherent plastics into a container, extracting the incoherent plastics from the container, reintroducing into the container at least one part of the incoherent plastics extracted from the container, detecting odorous emissions in a process gas exiting from the container, regulating the quantity of incoherent plastics reintroduced into the container on the basis of the aforesaid detection of odorous emissions.

BRIEF DESCRIPTION OF THE DRAWINGS

The invention can be better understood and implemented with reference to the attached drawings that illustrate some embodiments thereof by way of non-limiting example, in which:

FIG. 1 is a table showing, by way of example, the Odour Index (OR.I.) values for certain odorous substances;

DETAILED DESCRIPTION

Figure 2:
FIG. 2 shows a vertical raised diagram of a first embodiment of a deodorization apparatus for incoherent plastics made according to the present invention.

With reference to the aforesaid figures, identical elements of different embodiments have been indicated by the same numbering for greater simplicity and clarity. Overall with 1, a deodorization apparatus has been indicated for eliminating reducing or correcting an odour emanating from a substance, in particular from incoherent plastics, i.e. in the form of granules and/or microgranules and/or powder and/or flakes or the like. The deodorization apparatus 1 may be used, in particular, in a plant for treating incoherent plastics, such as for example a plant for dehumidification and/or drying and/or crystallization and/or vacuum conveying and/or pressure conveying of the incoherent plastics. The deodorization apparatus 1 may be arranged, in particular, in a process line (for example a continuous line) configured to process the incoherent plastics. The deodorization apparatus 1 may be arranged, for example, upstream of a dehumidification apparatus arranged to supply the dehumidified incoherent plastics to a user machine, such as for example an extruder that supplies extruded plastics to an injection and/or blow and/or compression moulding apparatus.

The deodorization apparatus may include in particular, at least one container 2 of the incoherent plastics. The container 2 may include for example, a hopper with a vertical extent. The container 2 may include in particular, at least one material inlet 3 for introducing incoherent plastics. The container 2 may include in particular, at least one material outlet 4 for extracting the incoherent plastics. The material inlet 3 may be arranged, as in these embodiments, in an upper portion of the container 2. The material outlet 4 may be arranged, as in these embodiments, in a lower portion of the container 2.

The container 2 may include in particular, at least one gas inlet 5 for introducing a process gas. The container 2 may include in particular, at least one gas outlet 6 for extracting the process gas. The gas outlet 6 may be arranged, as in these embodiments, in an upper portion of the container 2.

The deodorization apparatus 1 may include in particular, an actuator 7 for generating a flow of process gas (air) that enters the container 2 by the gas inlet 5 and exits from the container 2 by the gas outlet 6. The actuator 7 may include in particular, at least to one fan or blower.

The deodorization apparatus 1 may include in particular, an outlet olfactory sensor 8 arranged near the gas outlet 6 to detect and measure odorous emissions in the process gas exiting from the container 2.

The deodorization apparatus 1 may include in particular, a controller 9, in particular a programmable electronic control unit, for example an electronic processor or CPU. The controller 9 may be configured, in particular, to control the actuator 7 on the basis of signals supplied by the outlet olfactory sensor 8. The controller 9 may be configured, in particular, to control the actuator 7 so as to increase the flow of process gas if an odour intensity of the exiting process gas measured by the outlet olfactory sensor 8 is greater than or the same as a reference value.

The deodorization apparatus 1 may include in particular, at least one heater 10 arranged to heat the processing gas entering the container 2. The heater 10 may be arranged, in particular, near the gas inlet 5. The heater 10 may include in particular, an electric resistance. The controller 9 may be configured, in particular, to control the heater 10 on the basis of signals supplied by the outlet olfactory sensor 8. In particular, the controller 9 may be configured to control the heater 10 so as to increase the temperature of the entering process gas if an odour intensity of the exiting process gas measured by the outlet olfactory sensor 8 is greater than or the same as a reference value.

The deodorization apparatus 1 may include in particular, an inlet olfactory sensor 11 arranged to detect odorous emissions in the process gas entering the container 2. The olfactory sensors 8 and 11 may include in particular, an electronic nose configured to compare a detected odour with a set of predetermined and stored odours. In particular, the olfactory sensors 8 and 11 may include a set of sensors selected to detect predefined molecules, for example volatile organic compounds (VOC), hydrocarbons, alcohols, etc. In particular, the olfactory sensors 8 and 11 may include a set of sensors selected to detect, in particular, aromatic hydrocarbons and/or unsaturated hydrocarbons and/or saturated hydrocarbons and/or nitrogen esters and/or oxygenated compounds and/or sulphur compounds, etc.

In particular, the olfactory sensors 8 and 11 may include a set of sensors selected to detect, in particular, at least one, or at least two, or at least three, or at least four groups of substances selected from a group consisting of the following groups of substances: aromatic hydrocarbons, unsaturated hydrocarbons, saturated hydrocarbons, nitrogen esters, oxygenated compounds, sulphur compounds, etc. The olfactory sensors 8 and 11 may be configured, in particular, to detect at least two, or at least three, or at least four, or at least five substances selected from a set consisting of the following substances: methylbutene, benzene, toluene, pentene, propanethiol, etc.

The controller 9 may be configured, in particular, to control at least one process parameter of the apparatus 1 and/or at least one actuator of the apparatus 1 on the basis of signals supplied by the outlet olfactory sensor 8. The controller 9 may be configured, in particular, to control at least one process parameter of the apparatus 1 and/or at least one actuator of the apparatus 1 on the basis of signals supplied by the inlet olfactory sensor 11. The controller 9 may be configured, in particular, to control at least one process parameter of the apparatus 1 and/or at least one actuator of the apparatus 1 on the basis of signals supplied by the outlet olfactory sensor 8 and by the inlet olfactory sensor 11, for example on the basis of a difference between an odour intensity measured by the outlet olfactory sensor 8 and an odour intensity measured by the inlet olfactory sensor 11.

The controller 9 may be configured, in particular, to control the actuator 7 on the basis of signals supplied by the inlet olfactory sensor 11. The controller 9 may be configured, in particular, to control the heater 10 on the basis of signals supplied by the inlet olfactory sensor 11. The controller 9 may be configured, in particular, to control the actuator 7 on the basis of a difference between an odour intensity measured by the outlet olfactory sensor 8 and an odour intensity measured by the inlet olfactory sensor 11. The controller may be configured, in particular, to control the actuator 7 so as to increase the flow of process gas if the aforesaid difference of the odour intensity of the entering and exiting process gas is greater than or the same as a reference value.

The controller 9 may be configured, in particular, to control the heater 10 on the basis of a difference between an odour intensity measured by the outlet olfactory sensor 8 and an odour intensity measured by the inlet olfactory sensor 11. The controller may be configured, in particular, to control the heater 10 so as to increase the temperature of the entering process gas if the aforesaid difference of the odour intensity of the entering and exiting process gas is greater than or the same as a reference value.

The deodorization apparatus 1 may include in particular, a discharge device 12 configured to control a discharge of the incoherent plastics from the container 2 through the material outlet 4. The controller 9 may be configured, in particular, to control the discharge device 12 on the basis of signals supplied by the outlet olfactory sensor 8 and/or on the basis of signals supplied by the inlet olfactory sensor 11. In particular, the controller 9 may be configured to control the discharge device 12 so as to vary a dwell time of the incoherent plastics inside the container 2 on the basis of signals supplied by the outlet olfactory sensor 8. The controller 9 may be configured, in particular, to control the discharge device 12 so as to increase a dwell time of the incoherent plastics inside the container 2 if an odour intensity of the exiting process gas measured by the outlet olfactory sensor 8 is greater than or the same as a reference value. The controller 9 may be configured, in particular, to control the discharge device 12 so as to increase a dwell time of the incoherent plastics inside the container 2 if an odour intensity of the entering process gas measured by the inlet olfactory sensor 11 is greater than or the same as a reference value. The controller 9 may be configured, in particular, to control the discharge device 12 so as to increase a dwell time of the incoherent plastics inside the container 2 if the aforesaid difference of the odour intensity of the process gas measured entering and exiting from the container 2 is greater than or the same as a reference value.

It is possible, in particular, to increase the dwell time of the material in the container 2 (in any embodiment disclosed here), and thus to increase the deodorization treatment time, by an increase in the quantity or mass of material present in the container 2. This increase in quantity may be determined, in particular, by a sensor LC that detects, for example, the weight of the material present in the container 2, either by a sensor that detects the level of material present in the container 2, or by a sensor of another type.

The deodorization apparatus 1 may include in particular, a stirrer 13 arranged to mix the incoherent plastics contained in the container 2. The stirrer 13 may include in particular, at least one shaft that is rotatable by a motor 14. The stirrer 13 may include in particular, two or more blades 15 rotatable by a motor 14. The blades 15 may rotate, in particular, around a vertical rotation axis. The blades 15 may be arranged radially with respect to a rotation axis of the blades.

The controller 9 may be configured, in particular, to control the stirrer 13 on the basis of signals supplied by the outlet olfactory sensor 8. In particular, the controller 9 may be configured to increase a drive speed of the stirrer 13 if an odour intensity measured by the outlet olfactory sensor 8 is greater than or the same as a reference value.

The controller 9 may be configured, in particular, to control the stirrer 13 on the basis of signals supplied by the inlet olfactory sensor 11. In particular, the controller 9 may be configured to increase a drive speed of the stirrer 13 if an odour intensity measured by the inlet olfactory sensor 11 is greater than or the same as a reference value. The controller 9 may be configured, in particular, to control the stirrer 13 on the basis of a difference between an odour intensity measured by outlet olfactory sensor 8 and an odour intensity measured by the inlet olfactory sensor 11. In particular, the controller 9 may be configured to increase a drive speed of the stirrer 13 if a difference between the odour intensity measured by the outlet olfactory sensor 8 and by the inlet olfactory sensor 11 is greater than or the same as a reference value.

The deodorization apparatus 1 may include in particular, a temperature sensor T arranged to detect at least one temperature of the incoherent plastics in the container 2 and/or arranged to detect at least one temperature of the process gas in the flow generated by the actuator 7. The temperature sensor T may include in particular, at least one proximal temperature sensor, to detect at least one temperature of the incoherent plastics in the container 2 in a point nearer the material inlet 3, and at least one distal temperature sensor, to detect at least one temperature of the incoherent plastics in the container 2 in a point further from the material inlet 3.

The temperature sensor T may include in particular, one or more intermediate temperature sensors arranged to detect one or more temperatures of the incoherent plastics in one or more points of the path of the material in the container 2 included between the proximal temperature sensor and the distal temperature sensor.

The temperature sensor T may include in particular, at least one sensor arranged to detect at least one temperature of the process gas before the container 2 and before the heater 10. The temperature sensor T may include in particular, at least one sensor arranged to detect at least one temperature of the process gas that enters the container 2 after the heater 10 (in particular near the gas inlet 5). The temperature sensor T may include in particular, at least one sensor arranged to detect at least one temperature of the process gas that exits from the container 2.

The controller 9 may be configured, in particular, to control the stirrer 13 on the basis of signals supplied by the temperature sensor T. In particular, the controller 9 may be configured to increase a drive speed (for example a rotation speed) of the stirrer 13 if at least one temperature of the incoherent plastics in the container 2 measured by the temperature sensor T is greater than or the same as a reference value. In particular, the controller 9 may be configured to increase a drive speed (for example a rotation speed) of the stirrer 13 if a difference between at least two temperatures of the incoherent plastics measured by two different temperature sensors in the container 2 is greater than or the same as a reference value.

In particular, the controller 9 may be configured to increase a drive speed of the stirrer 13 if a difference between a temperature measured by the proximal temperature sensor and a temperature measured by the distal temperature sensor is greater than or the same as a reference value.

In particular, the controller 9 may be configured to increase a drive speed of the stirrer 13 if a difference between a temperature measured by the proximal temperature sensor and a temperature measured by an intermediate temperature sensor is greater than or the same as a reference value.

In particular, the controller 9 may be configured to increase a drive speed of the stirrer 13 if a difference between a temperature measured by the distal temperature sensor and a temperature measured by an intermediate temperature sensor is greater than or the same as a reference value.

In particular, the controller 9 may be configured to increase a drive speed of the stirrer 13 if a difference between at least two temperatures measured by two intermediate temperature sensors is greater than or the same as a reference value.

The deodorization apparatus 1 may include in particular, a recirculation device 16 configured to reintroduce into the container 2 at least one part of the incoherent plastics that is extracted from the container 2. The recirculation device 16 may be configured, in particular, to raise the incoherent plastics from an outlet section of the container 2 to an inlet section of the container 2, in which the inlet section is at a greater height than the outlet section. The recirculation device 16 may include in particular, at least one conveying system configured to convey incoherent material from an outlet section to an inlet section of the container 2. The conveying system may include for example, a conveying conduit, a lifting device, or other systems (in particular of known type, a spiral, pneumatic, aero-mechanical feed screw, etc) suitable for conveying incoherent material.

The deodorization apparatus 1 may be so configured as to recirculate all the exiting material, or so as to recirculate only a part of the exiting material whereas another part is moved away and/or sent for further processing. The deodorization apparatus 1 may be so configured as to recirculate the material more than once, for example a number of preset times or a number of times set by a feedback control system. The controller 9 may be configured, in particular, to control the recirculation device 16 on the basis of signals supplied by the outlet olfactory sensor 8. In particular, the controller 9 may be configured to control the recirculation device 16 so as to increase the recirculating flow, i.e. the flow of the incoherent plastics that is extracted from the container 2 and is returned to the container the container 2, if an odour intensity measured by the outlet olfactory sensor 8 is greater than or the same as a reference value.

The controller 9 may be configured, in particular, to control the recirculation device 16 on the basis of a difference between an odour intensity measured by the outlet olfactory sensor 8 and an odour intensity measured by the inlet olfactory sensor 11. In particular, the controller 9 may be configured to control the recirculation device 16 so as to increase the recirculated flow of the incoherent plastics, i.e. extracted from the container 2 and returned to the container 2, if the aforesaid difference between the odour intensity of the measured exiting process gas and measured entering process gas is greater than or the same as a reference value.

The controller 9 may be configured, in particular, to control the recirculation device 16 on the basis of the temperatures of the material detected by a plurality of temperature sensors T placed along the vertical development of the container 2, i.e. on the basis of a vertical profile of the temperature. The controller 9 may be configured, in particular, to control the recirculation device 16 so as to reach or maintain a given heat gradient along the vertical, for example a constant heat gradient (with a substantially linear trend of the temperature of the material along the vertical of the container 2). This permits substantially uniform extraction of the odour from the discharge zone of the treated material (material outlet 4) to the loading zone of the material to be treated (material inlet 3).

Figure 3:
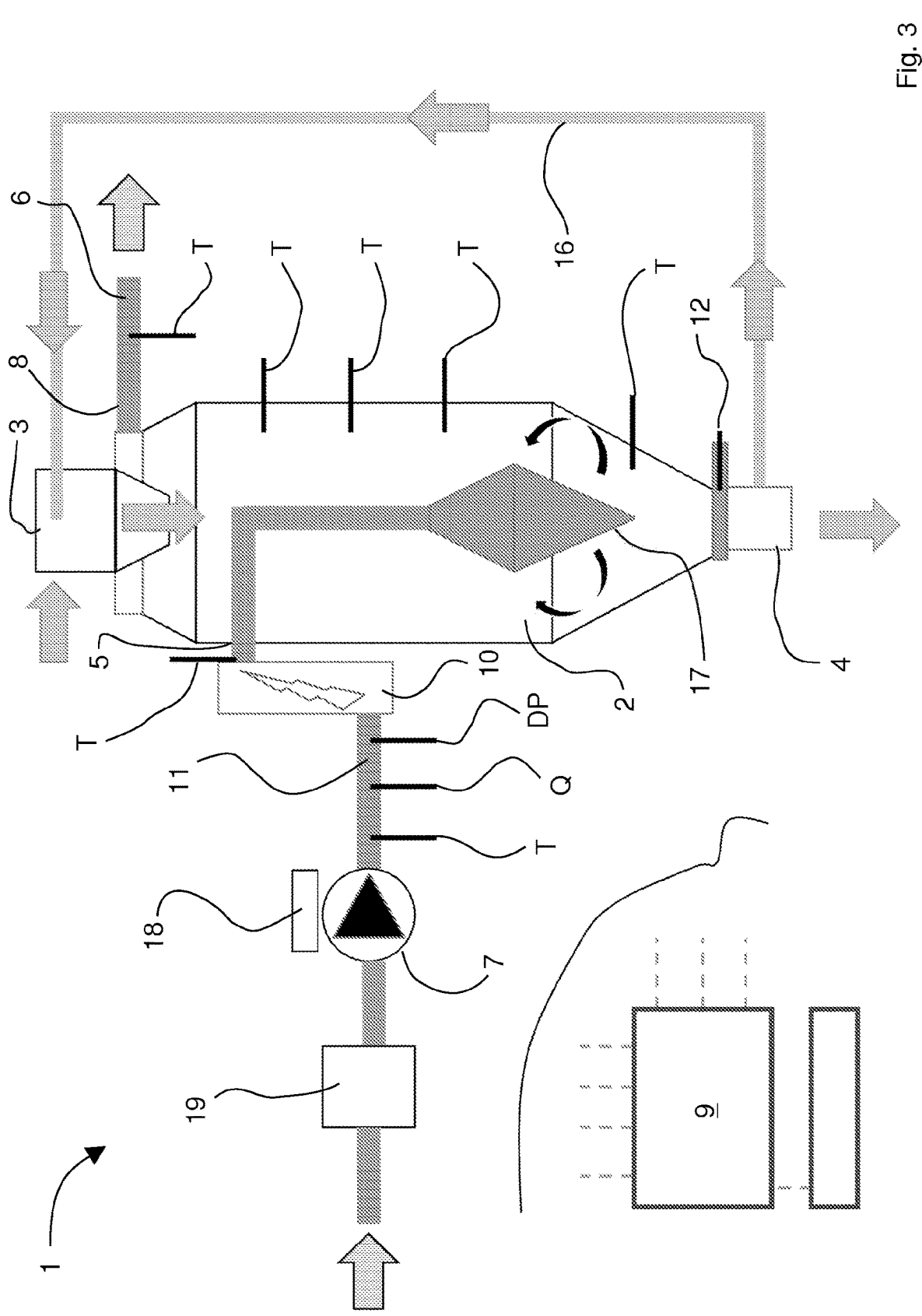
FIG. 3 shows a vertical raised diagram of a second embodiment of a deodorization apparatus for incoherent plastics made according to the present invention.

The deodorization apparatus 1 may include in particular, a diffuser 17 to diffuse the process gas inside the container 2. The diffuser 17 may include as in the embodiments of FIGS. 2 and 3, a diffuser arranged in a lower zone of the container 2, near the material outlet 4. The diffuser may include in particular, a plurality of outlets of the process gas to permit even distribution of the process gas that, starting from the lower zone of the container 2, will go to the gas outlet 6 arranged above. These outlets may be arranged, for example, circumferentially around an axis of the container 2. The diffuser may be connected, in particular, to the gas inlet 5 through a conveying circuit that conveys the gas to the diffuser downwards.

Figure 4:
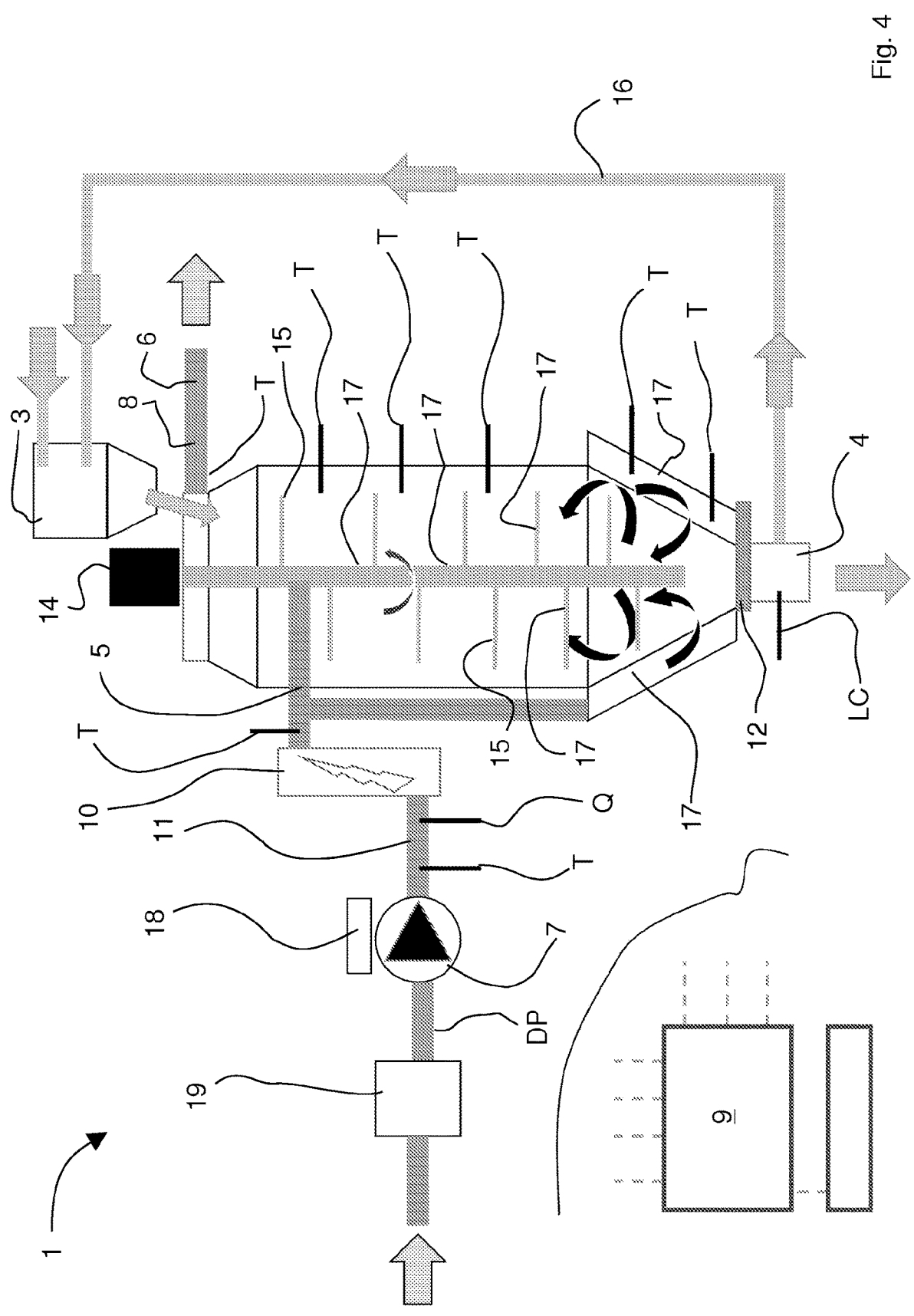
FIG. 4 shows a vertical raised diagram of a third embodiment of a deodorization apparatus for incoherent plastics made according to the present invention.

The diffuser 17 may include as in the example of FIG. 4, two or more process gas outlets arranged on the stirrer 13. The diffuser 17 may include in particular, two or more process gas outlets arranged on a rotation shaft of stirrer 13. The diffuser 17 may include in particular, two or more process gas outlets arranged on each blade of the stirrer 13. The diffuser 17 may include in particular, at least one rotating joint (for example of known and non-illustrated type) for the passage of the process gas from a fixed structure (for example a conveying circuit of the process gas connected to the gas inlet 5) to a rotating structure (for example the shaft of the stirrer 13).

The diffuser 17 may include a plurality of outlets of the process gas arranged in a lower portion of the container 2 (for example outlets including emission holes obtained on a wall of the lower portion of the container 2). In this case (see example of FIG. 4), the diffuser 17 includes an annular volume that surrounds a lower portion of the container 2 that includes a permeable wall (for example drilled) through which the process gas flows to increase the deodorization effect.

Each type of diffuser 17 disclosed here (with outlets arranged on the shaft of the stirrer 13, or on the blades 15, or on the wall of the container 2) may be used singly or in combination with one or more of the other types, in the presence or in the absence of the stirrer 13 and/or of the recirculation device 16.

The deodorization apparatus 1 may include in particular, an adjusting device for opening or closing selectively the gas outlets so as to adjust the diffusion of the process gas inside the container 2. This adjusting device may include in particular, choking of the flow of process gas diffused by the diffuser 17, for example by a dividing circuit and a controllable valve so as to increase or reduce choking. Choking may include for example, a valve system to control independently the gas outlets arranged on the shaft of the stirrer 13 and the gas outlets arranged on the blades of the stirrer 13.

The selective adjusting device for adjusting the gas outlets may be controlled, in particular, through feedback on the basis of signals supplied by the outlet olfactory sensor 8 and/or on the basis of signals supplied by the inlet olfactory sensor 11. The selective adjusting device for adjusting the gas outlets may be controlled, in particular, so as to increase the flow, increasing the number of open gas outlets, if an odour intensity measured by the outlet olfactory sensor 8 is greater than or the same as a reference value. The selective adjusting device for adjusting the gas outlets may be controlled, in particular, so as to increase the flow, increasing the number of open gas outlets, if an odour intensity measured by the inlet olfactory sensor 11 is greater than or the same as a reference value. The selective adjusting device for adjusting the gas outlets may be controlled, in particular, so as to increase the flow, increasing the number of open gas outlets, if a difference between the odour intensity measured by the outlet olfactory sensor 8 and by the inlet olfactory sensor 11 is greater than or the same as a reference value.

The deodorization apparatus 1 may include in particular, at least one dew point sensor DP of the process gas. The deodorization apparatus 1 may include in particular, at least one adjuster 18 of the actuator 7 (for example an inverter for the fan). The deodorization apparatus 1 may include in particular, at least one flowrate sensor Q to measure the flow of process gas. The deodorization apparatus 1 may include in particular, at least one level sensor to measure the level of incoherent plastics in the container 2. The deodorization apparatus 1 may include in particular, at least one filter 19 arranged to filter the process gas. The deodorization apparatus 1 may include in particular, at least one timer for monitoring treatment time.

In the illustrated embodiments, the circuit of the process gas includes an open circuit, where the process gas may include in particular, air removed from the environment and returned to the environment after the deodorization process. In other embodiments that are not illustrated, the circuit of the process gas may include a closed circuit, where the gas coming from the gas outlet 6 is purified (for example by active carbon filters or other purifying devices) of the odorous molecules extracted from the material and is returned to the container 2 through the gas inlet 5.

It is possible to provide a dehumidification and/or drying and/or crystallization apparatus for incoherent plastics (granular polymer resin) including a deodorization apparatus, made in accordance with the present invention, configured to extract the odours from the incoherent plastics.

The operation of the deodorization apparatus 1 involves heating the process gas in a controlled manner so that the temperature of the processed incoherent plastics does not exceed a desired or preset safety value.

The operation of the deodorization apparatus 1 may involve, in particular, heating the process gas in a controlled manner so that the quantity of heat yielded by the process gas, and then absorbed by the incoherent plastics, does not exceed a desired and preset maximum value and/or does not fall below a desired and preset minimum value.

The operation of the deodorization apparatus 1 may involve, in particular, generating a flow of the process gas with a controlled flowrate so that the quantity of heat yielded by the process gas, and then absorbed by the incoherent plastics, is the same as a set desired value (or around this value).

The operation of the deodorization apparatus 1 may involve, in particular, generating a flow of the process gas with a controlled flowrate so that the odour intensity of the process gas exiting from the container 2 is eliminated or anyway reaches a set desired minimum value, or as an absolute value, or in relation to the value of the odour intensity of the process gas entering the container 2. In practice, on the basis of laboratory tests, it has been found that an increase in the flow of the process gas improves the efficacy of the evacuation of the odorous molecules from incoherent plastics.

The deodorization apparatus 1 enables the actual quantity of odorous emissions released by the incoherent plastics to be detected in real time precisely and reliably. The deodorization apparatus 1 enables the actual quantity of residual odour in the plastics to be detected in real time precisely and reliably, for example on the basis of the difference of the odorous emissions measured in the process gas entering and exiting the container 2.

The olfactory sensor may be characterized and calibrated in such a way as to detect the odorous emissions required for the specific deodorization process, in particular on the type of material and/or the type of final use.

The deodorization apparatus 1 enables the material in the container 2 to be mixed or stirred so as to promote removal of the odour. The mixing function may be obtained, for example by the stirrer 13 of mechanical type, with a series of blades 15 or spokes that are radials and integral with a shaft with vertical rotation axis, which induce a mixing force of granules of plastic. The action of mixing may be conducted in different ways, for example by using a gas (for example the same process gas) delivered into the container 2 with great turbulence as a mixing agent, or by combining the two systems or with still other systems.

The deodorization apparatus 1 enables at least one part of the material to be recirculated, by removing a quantity (for example controlled and predefined) of material (resin granules) from a discharge del container 2 and returning this quantity to an inlet of the container 2, improving the efficacy of cleaning and/or extracting the odour.

In use, the plastics, in the form of granules and/or micro-granules and/or powder and/or flakes or the like, is introduced (in a known manner) into the container 2 (treatment hopper and/or silos). The container 2 includes one or more inlet sections and one or more outlet sections of the material. In these embodiments, the movement of the material from the inlet to the outlet occurs by gravity, so that the container 2 is positioned with a vertical axis, even if it is possible to provide other types of container, for example with a horizontal and movement axis of the material by conveying feed screw or the like.

The heating device (heater 10) heats the process gas to a desired temperature before introducing the process gas into the container 2. The diffuser 17 distributes uniformly and homogeneously the process gas inside the container 2 (in particular defining a main motion from bottom to top of the process gas inside the container 2) so as to affect the entire mass of the material.

As said, the actuator 7 may include a fan, or a blower, or other device that is able to generate a flow of air, in the specific embodiments by aspirating the air from the environment.

As visible in the figures, the temperature sensor T may be arranged in various points of the apparatus. In particular, the container 2 may be provided with two, three, four or more temperature sensors (probes) positioned at different heights to monitor the distribution of the temperature in the volume of the container 2, in particular to detect the heat profile of the mass of material in the container 2.

This has been disclosed with reference to one of the illustrated embodiments, may be present also in the other embodiments. In particular, the various sensors (temperature, dew point, flowrate, etc) disclosed above may be arranged in all the embodiments, further, the control logics implemented by the controller 9 may be configured to operate in all the embodiments.

The olfactory sensor, which is suitable for detecting the odorous emissions, is configured to detect the specific substances to be monitored, as a function of the type of use of the deodorization apparatus 1, in particular according to the chemical and physical characteristics of the incoherent plastics that has to be processed.

The various actuators and sensors of the deodorization apparatus 1 are connected to the controller 9 that may include in particular, at least one control unit (CPU), a PLC, a microprocessor, etc.

The controller 9 may include in particular, the computer programming instructions that are suitable for the operation of the deodorization apparatus 1 and thus for implementing the deodorization method in question.

The controller 9 may include in particular, a databank and/or a series of parameter indications (or "recipe") that enables the operator to select the type of polymer material and/or the mixture of materials to be treated. This series of indications of parameters (or "recipes") is located and stored, thus enabling the correct configuration to be set for the monitoring to be performed by the olfactory sensor, in particular for recognizing the odorous emissions typical of a certain material or mixture of materials.

On the basis of this selection of the type of polymer material and/or mixture of materials to be treated, it is possible to set at least one desired temperature of the process gas and a desired flowrate of the process gas. It is also possible to set a desired dwell time of the plastics (granule) inside the container 2. It is further possible to set a desired number of recirculation cycles for the material to obtain an appropriate level of decoration. It is also possible to set a desired driving speed of the stirrer 13.

The controller 9 is so programmed as to increase the flow of the process gas and, if possible, increase the temperature of the process gas, if the olfactory sensor detects insufficient elimination of the odorous emissions.

The diffuser 17, as said, may include outlets (for example consisting of emission holes) for the process gas, in particular distributed over movable portions (rotating shaft and/or rotating blades or spokes) of the stirrer 13. It is also possible to diffuse a flow of process gas (air) over the material, in particular a second flow of process gas, emitted through movable outlets, in addition to a main flow emitted through static outlets of the process gas, so as to increase the efficiency of the process of eliminating the odorous emissions.

As said, the flow of process gas that traverses the inside of the container to flow through the material may be choked, and choking may be adjusted, by the selective opening of different outlets of the process gas, in function of the level of the odorous emissions detected by the olfactory sensor. It is pointed out that the deodorization apparatus 1 may include a feedback control system for controlling the stirrer of the material, taking account of actual process conditions, in particular taking account of the temperature of the material and of the odour intensity of the process gas. It is further pointed out that owing to the recirculation of the material and/or the stirring of the material, it is possible to maintain the material moving and to avoid sticking and agglomeration phenomena owing to the presence of an amorphous structure.

The temperature sensor may include one or more temperature sensors arranged to measure the temperature of the incoherent plastics in the recirculation path of the material. Also the signals supplied by the latter one or more temperature sensors may be used in a feedback control system for controlling the stirrer 13 and/or the discharge device 12 and/or the recirculation device 16.

It is pointed out that the selective activation of a secondary flow of the process gas, if the apparatus has this option, enables dilution of the odorous emissions to be increased. This can improve the ability of the outlet olfactory sensor 8 to determine the efficacy of the deodorization action.

Figure 5:
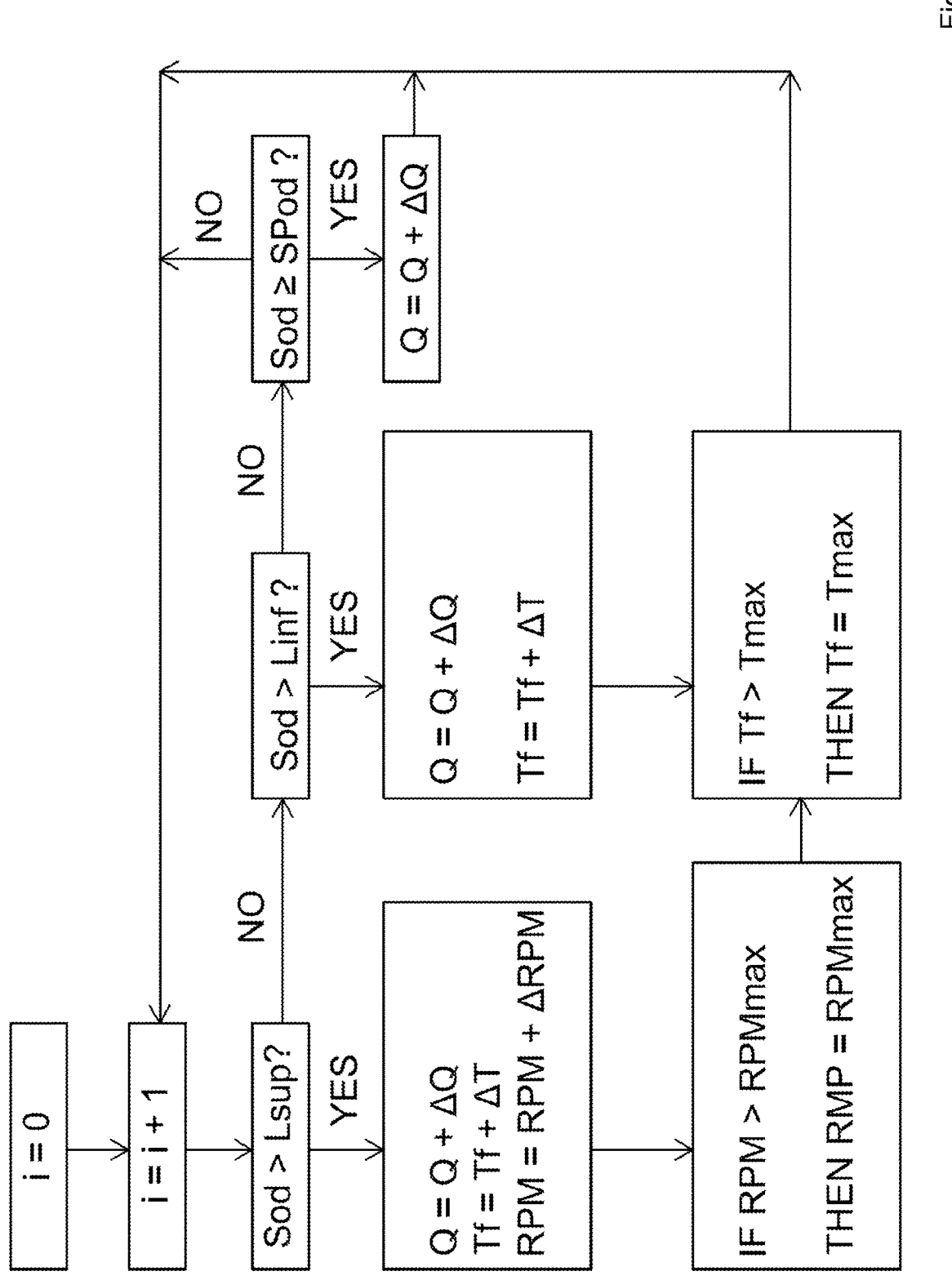
FIG. 5 shows a block diagram of an embodiment of an algorithm usable in a deodorization method made according to the present invention, in particular implementable on the controller of any one of the deodorizing apparatuses of FIGS. 2-4.

The diagram of FIG. 5 is one purely indicative and non-limiting embodiment of the invention, of an algorithm that is implementable on the electronic controller of the apparatus. The algorithm is of interactive type and the number of interaction cycles may be interrupted, in particular, at the interruption of the process or the switching off of the apparatus. The start of each interaction cycle may be determined, in particular, on a temporal basis, so that the $i^{th}$ interaction cycle can start after a set period of time (for example 30 seconds, or 1 minute, or 5 minutes, or 10 minutes, or 20 minutes, or 30 minutes, or 60 minutes, etc) from the preceding $(i-1)^{th}$ interaction cycle. The algorithm may control, in particular, one or more parameters, for example parameters chosen from the group that includes: the flowrate of the process gas Q, the temperature of the process gas Tf, the rotation speed RPM of the stirrer 13, the quantity of material recirculated by the recirculation device 16. It is possible to provide algorithms that control only one of the aforesaid parameters, or two of the aforesaid parameters (in any possible combination), or three of the aforesaid parameters (in any possible combination), or all four of the aforesaid parameters. Control of other parameters and/or other relative actuators may be provided.

In the example of FIG. 5, the algorithm controls Q, Tf and RPM. The algorithm of FIG. 5 uses two limit values of the odour, Linf and Lsup, in which SPod<Linf<Lsup, where SPod is a setpoint value of the odour of the process gas at the outlet. If the measured value Sod of the odour of the process gas at the outlet is less than SPod, the control does not modify any parameter. If the measured value Sod is included between SPod and Linf, the control intervenes on a parameter (in particular Q, as in the example of FIG. 5). If the measured value Sod is included between Linf and Lsup, the control intervenes on two parameters (in particular Q and Tf, as in the example of FIG. 5). If the measured value Sod is greater than Lsup, the control intervenes on three parameters (in particular Q, Tf and RPM, as in the example of FIG. 5). The values SPod, Linf, Lsup, $\Delta$T, Tmax, $\Delta$RPM and RPMmax, and the initial values of Q, Tf and RPM, are preset and stored.

It is possible to provide algorithms that store three limit values of the odour (in addition to the setpoint value SPod), in particular to control four parameters. It is possible to provide algorithms that store only one limit value of the odour (in addition to the setpoint value SPod), in particular to control two parameters. It is possible to provide algorithms that do not store any limit value of the odour (in addition to the setpoint value SPod), in particular to control a single parameter. Further, it is possible to use decremental values $\Delta$Q, $\Delta$T and $\Delta$RPM, to decrease the relative controlled parameter, if the measured value Sod is less than SPod, possibly using limit values of the odour below SPod, with an identical logic to the one disclosed above with reference to limit values of the odour above SPod.

LEGEND

1 Deodorization apparatus for deodorizing incoherent plastics
2 Container of the incoherent plastic material
3 Material inlet
4 Material outlet
5 Process gas inlet
6 Process gas outlet
7 Actuator for generating a process gas flow
8 Outlet olfactory sensor
9 Programmable electronic controller
10 Heater
11 Inlet olfactory sensor
12 Discharge device
13 Stirrer
14 Motor of stirrer
15 Blades of stirrer
16 Recirculation device of the incoherent plastic material
17 Diffuser of the process gas in the container
18 Adjuster of the actuator of the flow of process gas
19 Filter of the process gas
T Temperature sensor of the material and of the process gas
Q Flowrate sensor of the flow of process gas
DP Sensor of dew point of the process gas
LC Sensor of weight of the material in the container
i Number of the interaction cycle of the algorithm
Sod Value of odour read by the outlet olfactory sensor
SPod Setpoint of the odour value (desired odour)
Linf Lower limit of the odour value (Linf>SPod)
Lsup Upper limit of the odour value (Lsup>Linf)
Tf Desired temperature of the process gas at the inlet
$\Delta$T Temperature delta (to be increased or decreased)

Tmax Maximum temperature of the process gas at the inlet

Q Desired flowrate of the process gas

ΔQ Flowrate delta of the process gas (to be increased or decreased)

RPM Desired rotation speed of the stirrer

ΔRPM Rotation speed delta of the stirrer (to be increased or decreased)

RPMmax Maximum rotation speed of the stirrer

The invention claimed is:

1. Deodorization apparatus to eliminate, reduce or correct an odor of an incoherent plastic material, the apparatus including:

at least one container with at least one material inlet for introducing the incoherent plastic material;

at least one material outlet for extracting the incoherent plastic material;

at least one gas inlet for introducing a process gas;

at least one gas outlet for extracting the process gas;

an actuator for generating a process gas flow which enters the gas inlet and exits from the gas outlet;

an outlet olfactory sensor arranged at the gas outlet to detect odorous emissions within the process gas exiting from the container after processing the incoherent plastic material in the container; and a controller configured to control the apparatus on a basis of signals provided by the outlet olfactory sensor, wherein:

when the odorous emissions are detected by the outlet olfactory sensor, the controller is configured to control the actuator to remove the odorous emissions.

2. The apparatus according to claim 1, wherein:

the controller is configured to control at least one process parameter on the basis of signals provided by the outlet olfactory sensor;

the at least one process parameter including at least one operating parameter of the process gas flow; and the at least one operating parameter including a flow rate of the process gas flow and/or a temperature of the process gas flow.

3. The apparatus according to claim 1, wherein:

the controller is configured to control the actuator on the basis of signals provided by the outlet olfactory sensor; and the controller being configured to control the actuator so as to increase a flow of the process gas if an odor intensity measured by the outlet olfactory sensor is greater than or equal to a reference value.

4. The apparatus according to claim 1, including:

at least one heater arranged to heat the process gas entering the container, wherein:

the controller being configured to control the at least one heater on the basis of signals provided by the outlet olfactory sensor; and the controller being configured to control the at least one heater so as to increase of the process gas if an odor intensity measured by the outlet olfactory sensor is greater than or equal to a reference value.

5. The apparatus according to claim 1, including:

an inlet olfactory sensor arranged to detect odor emissions in the process gas entering the container, wherein:

the controller being configured to control the actuator on the basis of signals provided by the inlet olfactory sensor; and the controller being configured to control the actuator on the basis of a difference between an odor intensity measured by the outlet olfactory sensor and an odor intensity measured by the inlet olfactory sensor.

6. Apparatus The apparatus according to claim 1, including, a discharge device configured to control a discharge of the incoherent plastic material through the material outlet, wherein:

the controller being configured to control the discharge device on the basis of signals provided by the outlet olfactory sensor;

the controller being configured to control the discharge device so as to vary a dwell time of the incoherent plastic material inside the container on the basis of signals provided by the outlet olfactory sensor; and the controller being configured to increase a dwell time of the incoherent plastic material inside the container if an odor intensity measured by the outlet olfactory sensor is greater than or equal to a reference value.

7. The apparatus according to claim 1, including:

a stirrer configured to stir the incoherent plastic material in the container, wherein:

the controller being configured to control the stirrer on the basis of signals provided by the outlet olfactory sensor;

the controller being configured so as to increase a speed of the stirrer if an odor intensity measured by the outlet olfactory sensor is greater than or equal to a reference value;

the stirrer including at least one shaft rotatable by a motor and/or two or more paddles which can be rotated by a motor.

8. The apparatus according to claim 7, including, an inlet olfactory sensor arranged to detect the odorous emissions in the process gas entering the container, wherein, the controller being configured to control the stirrer based on signals supplied by the inlet olfactory sensor;

the controller being configured to control the stirrer on a basis of a difference between an odor intensity measured by the outlet olfactory sensor and an odor intensity measured by the inlet olfactory sensor; and the controller being configured so as to increase a speed of the stirrer if a difference between an odor intensity measured by the outlet olfactory sensor and an odor intensity measured by the inlet olfactory sensor is greater than or equal to a reference value.

9. Apparatus The apparatus according to claim 1, including:

a stirrer configured for stirring the incoherent plastic material in the container; and a temperature sensor arranged to detect at least one temperature of the incoherent plastic materials in the container, wherein:

the controller being configured to control the stirrer on the basis of signals provided by the temperature sensor;

the controller being configured to increase a speed of the stirrer if a temperature measured by the temperature sensor is greater than or equal to a value of reference;

the temperature sensor including at least one proximal temperature sensor closer to the material inlet and at least one distal temperature sensor more distant from the material inlet; and the controller being configured to increase a speed of the stirrer if a difference between a temperature measured by the proximal temperature sensor and a temperature measured by the distal temperature sensor is greater than or equal to a reference value.

10. The apparatus according to claim 1, including:

a recirculation device for reintroducing into the container at least a part of the incoherent plastic material extracted from the container, wherein:

the controller being configured for controlling the recirculation device on the basis of signals supplied by the outlet olfactory sensor;

the recirculation device being configured to lift the incoherent plastic material from an outlet section of the container to an inlet section of the container:

the inlet section is at a higher altitude than the outlet section;

the recirculation device including at least one material transport conduit included between the outlet section and the inlet section; and the controller being configured to control the recirculation device so as to increase the incoherent plastic material extracted from the container and reintroduced into the container if an odor intensity measured by the outlet olfactory sensor is greater than or equal to a reference value.

11. The apparatus according to claim 10, including:

an inlet olfactory sensor arranged to detect the odorous emissions in the process gas entering the container, wherein:

the controller being configured to control the recirculation device based on a difference between an odor intensity measured by the outlet olfactory sensor and an odor intensity measured by the inlet olfactory sensor; and the controller being configured to control the recirculation device so as to increase the incoherent plastic materials extracted from the container and reintroduced into the container if the difference between an outlet odor intensity and an inlet odor intensity is greater than or equal to a reference value.

12. The apparatus according to claim 1, including:

a recirculation device for reintroducing into the container at least a part of the incoherent plastic material extracted from the container; and a temperature sensor arranged to detect at least one temperature of the incoherent plastic material in the container, wherein:

the controller being configured to control the recirculation device based on signals provided by the temperature sensor; and the controller being configured so as to increase the incoherent plastic material extracted from the container and reintroduced into the container if at least one temperature or a difference of temperatures detected by the temperature sensor is greater than or equal to a reference value.

13. Deodorization apparatus to eliminate, reduce or correct an odor of an incoherent plastic material, the apparatus including:

at least one container with at least one material inlet for introducing incoherent plastic material;

at least one material outlet for extracting the incoherent plastic material;

at least one gas inlet for introducing a process gas;

at least one gas outlet to extract the process gas;

an actuator for generating a process gas flow which enters the gas inlet and exits from the gas outlet;

an outlet olfactory sensor arranged at the gas outlet to detect odorous emissions within the process gas exiting from the container processing the incoherent plastic material in the container; and an inlet olfactory sensor arranged to detect odorous emissions in the process gas entering the container, wherein;

when the odorous emissions are detected by the outlet olfactory sensor, a controller is configured to control the actuator to remove the odorous emissions.

14. The apparatus according to claim 13, including:

a stirrer configured to stir the incoherent plastic material in the container, and a diffuser for diffusing the process gas inside the container wherein:

the diffuser including two or more process gas outlets arranged on the stirrer;

the stirrer including at least one shaft which can be rotated by a motor and/or two or more paddles which can be rotated by a motor and which can be rotated about a vertical rotation axis;

the gas outlets being arranged on the shaft and/or on the paddles;

the apparatus including an adjustment device for selectively opening or closing the gas outlets so as to regulate the diffusion of the process gas inside the container;

the apparatus including the controller configured to feedback control the adjustment device of the diffuser based on signals provided by the outlet olfactory sensor and/or by the inlet olfactory sensor;

the controller being configured to feedback control the adjustment device of the diffuser based on a difference between an odor intensity measured by the outlet olfactory sensor and an odor intensity measured by the inlet olfactory sensor; and the controller being configured to control the adjustment device of the diffuser so as to increase a flow of process gas delivered by the diffuser if a difference between an odor intensity measured by the outlet olfactory sensor and an odor intensity measured by the inlet olfactory sensor is greater than or equal to a reference value.

15. The apparatus according to claim 14, including:

a temperature sensor arranged to detect at least one temperature of the process gas exiting from the container; and the controller configured to feedback control the adjustment device of the diffuser based on signals provided by the temperature sensor so as to decrease a flow of process gas delivered by the diffuser if a measured temperature of the process gas exiting from the container is higher than a reference value.

16. The apparatus according to claim 13, including:

a recirculation device configured to reintroduce at least a part of the incoherent plastic material extracted from the container into the container, wherein:

the recirculation device being configured to life the incoherent plastic material from an outlet section of the container to an inlet section of were the container, where the inlet section is at a height higher than the outlet section; and the recirculation device including at least one conduit or one material transport element included between the outlet section and the inlet section.

* * * * *